(12) United States Patent
Lok

(10) Patent No.: US 6,730,500 B1
(45) Date of Patent: May 4, 2004

(54) METHODS FOR GENERATING A CONTINUOUS NUCLEOTIDE SEQUENCE FROM NONCONTIGUOUS NUCLEOTIDE SEQUENCES

(75) Inventor: Si Lok, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 36 days.

(21) Appl. No.: 09/938,077

(22) Filed: Aug. 23, 2001

Related U.S. Application Data

(60) Provisional application No. 60/257,079, filed on Dec. 20, 2000, and provisional application No. 60/229,109, filed on Aug. 30, 2000.

(51) Int. Cl.[7] ................................................. C12Q 1/68
(52) U.S. Cl. ..................................................... 435/91.2
(58) Field of Search ......................... 435/91.2; 536/23.1

(56) References Cited

U.S. PATENT DOCUMENTS 5,514,568 A * 5/1996 Stemmer ................... 435/91.2
6,261,797 B1 * 7/2001 Sorge et al. ................... 435/41
6,410,220 B1 * 6/2002 Hodgson et al. ................ 435/4

FOREIGN PATENT DOCUMENTS

EP         1 130 092     *  9/2001    ........... C12N/15/10

* cited by examiner

*Primary Examiner*—Kenneth R. Horlick
(74) *Attorney, Agent, or Firm*—Michelle L. Johnson; Phillip B.C. Jones

(57) ABSTRACT

The increased use of nucleotide sequence data mining techniques has amplified the demand for efficient methods of producing recombinant proteins in host cells. New genes identified from genomic sequences may lack an identified source for obtaining an mRNA template to produce cDNA. A strategy is provided for generating nucleic acid molecules comprising a continuous amino acid-encoding sequence using a genomic template that contains non-continuous amino acid-encoding sequences.

17 Claims, 1 Drawing Sheet

METHODS FOR GENERATING A CONTINUOUS NUCLEOTIDE SEQUENCE FROM NONCONTIGUOUS NUCLEOTIDE SEQUENCES

CROSS-REFERENCE TO RELATED APPLICATIONS

This application claims the benefit of U.S. Provisional application No. 60/229,109 (filed Aug. 30, 2000), and U.S. Provisional application No. 60/257,079 (filed Dec. 20, 2000), the contents of which are incorporated by reference.

TECHNICAL FIELD

The present invention relates generally to methods for producing recombinant nucleotide sequences from noncontiguous nucleotide sequences.

BACKGROUND OF THE INVENTION

An emerging class of genes is first discovered through interrogation of genomic databases. Many of these genes are not represented in the current expressed sequence tag databases, suggesting that they are expressed at very low levels per cell, by a limited number of cell types, or at restricted times. In the absence of information about a suitable source of mRNA template, conventional methods for isolating a full-length cDNA derived from such genes are of limited utility.

The provision of a nucleic acid molecule encoding a full-length polypeptide is a necessary first step for producing the polypeptide with recombinant technology. Although certain eukaryotic expression systems can produce recombinant proteins encoded by genomic sequences, many genes contain multiple introns with a collective length that renders the expression unit too large to be efficiently inserted into typical plasmid-based expression vectors. Moreover, the presence of repeated elements within intron sequences may promote plasmid-instability while the expression vector is being propagated within the bacterial host. The presence of intron sequences in an expression cassette also creates the possibility that recipient mammalian host cells will use cryptic splice donor and acceptor sites within the intron. The use of such alternative splice sites may be natural to the gene, or may create an artifact in the expression host cell. Thus, the use of these cryptic splice sites in the host cell may lead to the production of a different recombinant polypeptide then intended. The splicing mechanisms of mammalian, yeast, or insect cells may also be sufficiently different from each other to preclude accurate or efficient splicing of certain mRNA molecules transcribed by heterologous genes. Finally, the lack of mRNA splicing in bacterial host cells necessitates the removal of all intron sequences within the expression unit for the production of recombinant protein.

A particularly convenient method for the isolation of defined DNA segments uses the polymerase chain reaction (PCR) and suitable pairs of primers. While the use of PCR and pairs of exon-specific primers enables the isolation of exon gene segments, however, the joining of resulting exon segments to produce a contiguous polypeptide coding sequence is difficult.

A common method to join PCR generated DNA segments to other DNA segments uses a class II restriction endonuclease cleavage site near the 5' end of each member of the PCR primer pair. The resulting PCR product would incorporate the restriction endonuclease sites at its terminus, which, upon digestion, would produce suitable cohesive overhangs to promote efficient ligation in the presence of DNA ligase. This method, however, cannot be employed to ligate exon segments, or portions of exon segments, to produce a contiguous polypeptide coding sequence. Exon segments ligated together in this manner would contain a foreign restriction endonuclease recognition sequence between ligated segments, thereby introducing one or more added amino acid residues at each ligation junction.

At high DNA and DNA ligase concentrations, it is possible to ligate blunt-ended DNA segments together. The socalled blunt-end ligation reaction enables the ligation of PCR-generated exon segments without the need to incorporate restriction endonuclease sites to the primers, and, as a result, the ligated products are free of foreign sequences. This approach, however, has severe limitations as well. Since the blunt-end ligation reaction does not use defined cohesive ends, the number of combinations and permutations of incorrect ligation products increases exponentially with the number of exons to be ligated, rendering this method impractical for general use.

Hence, there is a need for a rapid and efficient method to convert an intron-containing gene sequence to a contiguous polypeptide coding sequence free of introns.

BRIEF SUMMARY OF THE INVENTION

The present invention provides improved methods for producing nucleic acid molecules, that encode an amino acid sequence of interest, or that comprise at least one regulatory sequence. According to one aspect of the present invention, an amino acid-encoding nucleic acid molecule with a continuous open reading frame is produced from noncontiguous amino acid-encoding nucleotide sequences.

These and other aspects of the invention will become evident upon reference to the following detailed description and the attached drawing. In addition, various references are identified below and are incorporated by reference in their entirety.

DESCRIPTION OF THE INVENTION

1. Overview

Figure 1:
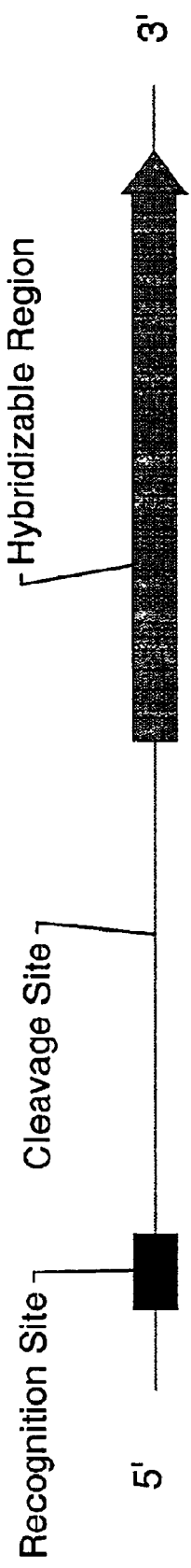
FIG. 1 shows an illustrative primer useful for methods of the present invention, which includes the following components (not drawn to scale): a class IIS restriction endonuclease recognition site, the cleavage site of the class IIS restriction endonuclease, and a region capable of hybridizing to a target molecule.

The present invention provides a new nucleic acid amplification method for generating exon fragments to produce a contiguous polypeptide coding sequence that is free of introns or other extraneous sequences. According to one aspect of the invention, specific primer pairs are designed to amplify each exon of a gene either from a genomic DNA template, or from genomic DNA inserts cloned in, for example, bacterial artificial chromosomes, P1-derived artificial chromosomes, or other vectors. Members of each exon-specific primer pair are synthesized with a suitable class IIS restriction endonuclease site in the appropriate orientation near its 5' terminus. As described below, the class IIS restriction enzymes cleave double-stranded DNA and generate complementary cohesive ends at a defined distance and direction outside an asymmetric DNA recognition site. In particular, a subset of the class IIS enzymes, which has an uninterrupted recognition sequence, can be exploited to design sets of exon-specific PCR primers. Digestion of the resulting amplified exon products produces cohesive overhangs consisting entirely of exon-derived sequences. To achieve the ligation of exon segments in the correct order and orientation, exon-primer-pairs can be designed such that adjacent exon segments have unique, but complementary, cohesive overhangs. In this way, ligation of a complex exon mixture can be achieved by cohesive end ligation in the correct orientation and order, without the addition of sequences encoding foreign amino acids. Such an artifact would be created if class II endonuclease sites are incorporated into the PCR primers.

As described herein, the present invention provides methods for producing a nucleic acid molecule that comprises a continuous nucleotide sequence of interest derived from noncontiguous nucleotide sequences, comprising:

(a) amplifying at least two nucleotide sequences from a nucleic acid molecule template using primer pairs to produce double-stranded amplified products, wherein the amplified nucleotide sequences reside noncontiguously in the nucleic acid molecule template, wherein each primer of a primer pair comprises a continuous recognition sequence for a class IIS restriction endonuclease which is located near the 5'-end of the primer, such that cleavage of the amplified products with the class IIS restriction endonuclease yields at least two nucleic acid molecule fragments with cohesive ends that, when ligated to each other, produce a continuous nucleotide sequence of interest, (b) cleaving amplified products with the class IIS restriction endonuclease to produce nucleic acid molecule fragments, and (c) ligating cleaved nucleic acid molecule fragments to produce a nucleic acid molecule comprising the continuous nucleotide sequence of interest.

The present invention also provides methods for producing a nucleic acid molecule that comprises a continuous nucleotide sequence of interest derived from noncontiguous nucleotide sequences, comprising:

(a) amplifying at least two nucleotide sequences from at least two nucleic acid molecule templates using primer pairs to produce double-stranded amplified products, wherein each primer of a primer pair comprises a continuous recognition sequence for a class IIS restriction endonuclease which is located near the 5'-end of the primer, such that cleavage of the amplified products with the class IIS restriction endonuclease yields at least two nucleic acid molecule fragments with cohesive ends that, when ligated to each other, produce a continuous nucleotide sequence of interest, (b) cleaving amplified products with the class IIS restriction endonuclease to produce nucleic acid molecule fragments, and (c) ligating cleaved nucleic acid molecule fragments to produce a nucleic acid molecule comprising the continuous nucleotide sequence of interest.

Suitable class IIS restriction endonuclease recognize a five-base, six-base, or seven-base continuous recognition sequence. Illustrative class IIS restriction endonucleases, which recognize a five-base continuous sequence include AclWI, Alw26I, AlwI, AsuHPI, BbvI, BcefI, BinI, BseGI, BseMII, BseXI, BspPI, BsmAI, Bst71I, BstF5I, FauI, FokI, HgaI, HphI, MboII, PleI, SfaNI, and TspRI. Exemplary class IIS restriction endonucleases, which recognize a six-base continuous sequence include AceIII, BbsI, BbvII, Bce83I, BciVI, BfiI, BfuI, BmrI, BpiI, BpmI, BpuAI, BsaI, Bse3DI, BseRI, BsgI, BsmBI, BsmFI, BspMI, BsrDI, Bsu6I, Eam1104I, EarI, Eco31I, Eco57I, Esp3I, FauI, GsuI, Ksp632I, MmeI, RleAI, TaqII, and Tth111II. SapI is an example of a class IIS restriction endonuclease, which recognizes a seven-base continuous recognition sequence.

The methods of the present invention can be performed with nucleic acid molecule templates that are genoric DNA, cDNA, vector DNA, a chemically-synthesized nucleic acid molecule, and the like.

The methods described herein can be used to produce amplified products comprising at least a portion of an exon, amplified products comprising a nucleotide sequence capable of controlling gene expression, amplified products, in which at least one of the amplified products comprises at least a portion of an exon, and at least one of the amplified products comprises a nucleotide sequence capable of controlling gene expression, as well as amplified products wherein at least one of the amplified products comprises at least one mutation of the nucleotide sequence that resides in the corresponding nucleic acid molecule template. Such a mutation, for example, can reside in an amino acid encoding sequence. Illustrative nucleotide sequences capable of controlling gene expression include regulatory elements, promoters, and downstream expression control elements.

For example, the methods described herein can be used to produce nucleic acid molecules, wherein the continuous nucleotide sequence of interest encodes an amino acid sequence, and wherein each of the amplified products comprises an exon. According to one approach, one primer of each primer pair is partially complementary to the antisense strand of the 5' end of an exon, and the other primer of each primer pair is partially complementary to the sense strand of the 3'-end of the exon.

The methods described herein can be used to produce nucleic acid molecules by ligating any number of nucleic acid molecule fragments. For example, nucleic acid molecules can be produced by ligating 25 to 50 nucleic acid molecule fragments, greater than 20 nucleic acid molecule fragments, 2 to 20 nucleic acid molecule fragments, 2 to 10 nucleic acid molecule fragments, 2 to 5 nucleic acid molecule fragments, or fewer than 5 nucleic acid molecule fragments.

Suitable amplification methods include a polymerase chain reaction, nucleic acid sequence based amplification, self-sustained sequence amplification, restriction amplification, strand displacement amplification, and the like.

The present invention further provides nucleic acid molecules suitable for performing various methods described herein. For example, the present invention provides an amplification primer, which comprises a continuous sequence of a class IIS restriction endonuclease recognition site near the 5'-end of the primer, and a nucleotide sequence capable of hybridizing with a nucleic acid molecule template, which is located downstream of the class IIS restriction endonuclease recognition to cleavage site. The class IIS restriction endonuclease recognition site typically resides between the 5'-end and the mid-point of the primer. The hybridizable nucleotide sequence can bind with an encoding region of a gene, or with a non-encoding target of interest, such as a regulatory sequence.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "structural gene" refers to a nucleic acid molecule that is transcribed into messenger RNA (mRNA), which is then translated into a sequence of amino acids characteristic of a specific polypeptide. A "gene of interest" can be a a structural gene.

In the context of a double-stranded DNA molecule comprising a gene, the term "upstream" refers to the direction that is toward the 5'-end of the DNA strand (the "antisense strand") complementary to the strand (the "sense strand") that serves as the template for transcription, whereas the term "downstream" refers to the opposite direction. As used herein, the terms "upstream" and "5'-ward" are used interchangeably, as are the terms "downstream" and "3'-ward."

"Complementary DNA (cDNA)" is a single-stranded DNA molecule that is formed from an mRNA template by the enzyme reverse transcriptease. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a CDNA molecule synthesized from an RNA template.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature. "Linear DNA" denotes non-circular DNA molecules with free 5' and 3' ends. Linear DNA can be prepared from closed circular DNA molecules, such as plasmids, by enzymatic digestion or physical disruption.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about ten amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the tppe of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasrids that are introduced into the cells by electroporation or other techniques. Integrated genetic elements are passed from the original host cell to its progeny.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector.

"Integrative transformants" are recombinant host cells, in which heterologous DNA has become integrated into the genomic DNA of the cells.

The term "expression" refers to the biosynthesis of a gene product. For example, in the case of a structural gene, expression involves transcription of the structural gene into MRNA and the translation of mRNA into one or more polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylarmide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

As used herein, the term "immunomodulator" includes cytokines, stem cell growth factors, lymphotoxins, co-stimulatory molecules, hematopoietic factors, and synthetic analogs of these molecules. Examples of immunomodulators include tumor necrosis factor, interleukins, colony stimulating factors, interferons, stem cell growth factors, erythropoietin, and thrombopoietin.

An "anti-idiotype antibody" is an antibody that binds with the variable region domain of an immunoglobulin.

An "antibody fragment" is a portion of an antibody such as $F(ab')_2$, $F(ab')_2$, Fab', Fab, and the like. Regardless of structure, an antibody fragment binds with the same antigen that is recognized by the intact antibody.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

A "fusion protein" is the product of combining at least two nucleotide sequences, which are normally noncontiguous. This type of hybrid protein can be encoded by a nucleic acid molecule that comprises nucleotide sequences of at least two genes. Alternatively, fusion proteins can be encoded by a nucleic acid molecule that comprises nucleotide sequences from one gene, wherein those nucleotide sequences are not contiguous in the naturally occurring form of the gene.

The term "antibody fusion protein" refers to a recombinant molecule that comprises an antibody, or antibody fragment, and a therapeutic agent. Examples of therapeutic agents suitable for such fusion proteins include immunomodulators ("antibody-immunomodulator fusion protein") and toxins ("antibody-toxin fusion protein"). Illustrative toxin components include a Pseudomonas exotoxin moiety, a diphtheria toxin moiety, an RNase moiety, a DNase I moiety, a gelonin moiety, and a Staphylococcal enterotoxin-A moiety.

The term "affinity tag" is used herein to denote a polypeptide segment that can he attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

Due to the imprecision of standard analytical methods, molecular weights and lengths of polymers are understood to be approximate values. When such a value is expressed as "about" X or "approximately" X, the stated value of X will be understood to be accurate to ±10%.

3. Production of a Nucleic Acid Molecule Containing a Contiguous Nucleotide Sequence of Interest Restriction endonucleases belong to three general classes. Class I restriction endonucleases cleave at widely varying distances from their recognition sites. Class II restriction endonucleases cleave within their recognition sites, while a subclass, class IIS, cleaves at precise distances outside of their recognition sites. Like class IIS enzymes, class m enzymes have separate recognition and cleavage domains. However, the class IIS restriction enzymes and methyltransferases are separate molecules, whereas class III molecules comprise a single multidomain moiety.

Since the recognition and cleavage sites are the same for class II enzymes and distinct for class IIS enzymes, the products of these two classes have different properties. Class II enzymes cleave within a symmetric recognition site, producing 5' to 3' sequences that are identical for both strands. For example, EcoRI cleaves as follows:

```
5'...G↓AATT-C...3'        5'...G   AATTC...3'
3'...C-TTAA↑G...5'   →    3'...CTTAA   G...5'
```

In contrast, a class IIS restriction endonuclease cleaves outside an asymmetric recognition site at a precise distance from the site. Due to this asymmetry, the 5' to 3' recognition sequences are different for each strand. For example, BstXI cleaves the following sequence, where "N" is any nucleotide:

```
5'...CCANNNNN↓NTGG...3'   (SEQ ID NO:5)
3'...GGTN↑NNNNNACC...5'   (SEQ ID NO:6)
            ↓
5'...CCANNNNN   NTGG...3'
3'...GGTN   NNNNNACC...5'.
```

The subset of class IIS restriction endonucleases most useful for the methods described herein are endonucleases that recognize an uninterrupted nucleotide sequence. For example, Eco31I cleaves the following sequence:

```
5'...GGTCTCN↓NNNNN...3'   (SEQ ID NO:7)
3'...CCAGAGNNNNN↑N...5'   (SEQ ID NO:8)
            ↓
5'...GGTCTCN   NNNNN...3'
3'...CCAGAGNNNNN   N...5'.
```

When DNA fragments containing these non-palindromic, or "rotationally nonequivalent," ends are ligated to each other, the fragments are inserted directionally. Thus, nucleic acid molecules comprising non-palindromic ends can be ligated together in a directional manner.

A. Design of Amplification Primers

The methods described herein can be used to produce a continuous nucleotide sequence from a source comprising non-continuous nucleotide sequences. The general approach is to amplify the nucleotide sequences of interest, and to ligate these amplified sequences in a directional manner. The amplification can be achieved by PCR, or any other well-known amplification method.

Amplification primers are designed to include a class IIS restriction endonuclease recognition site near the 5'-end. In this context, "near" refers to a position that resides between the 5'-end and the mid-point of the primer. For example, the recognition site can be placed "X" nucleotides from the 5'-end of the primer, wherein X is an integer selected from a range of 1 to 10 nucleotides (ie., 1, 2, 3, 4, 5, 6, 7, 8, 9, or 10), or X can be greater than ten nucleotides. A nuclcotide sequence capable of hybridizing with an intended target is located downstream of the endonuclease cleavage site. This hybridizable sequence may bind with an encoding region of a gene or a non-encoding target of interest, such as a regulatory sequence. Moreover, the hybridizable region may reside within a portion of the primer between the restriction endonuclease cleavage site and the 3'-end of the primer, as shown in FIG. 1, or may extend to at least one of the cleavage site and the 3'-end. Conveniently, mutations of a native nucleotide sequence can be introduced in the region between the cleavage site and the 3'-end of the primer. Such mutations can reside, for example, within the hybridizable region, as long as this region can bind to its target sequence.

A class IIS recognition site not only provides the advantage of directional cloning, but enables cleavage to occur at a position that is located at a defined distance from the recognition site. In this way, an amplified nucleic acid molecule that includes a non-naturally occurring class IIS recognition site can be cleaved to expose a nucleotide sequence of interest, such as a nucleotide sequence that encodes a portion of a particular amino acid sequence.

Suitable class IIS restriction enzymes include those enzymes that recognize a five-base contiguous sequence, such as the following enzymes and their isoschizomers, which are indicated in parentheses: Alw26I (BsmAI), AlwI (AclWI, BinI), AsuHPI (HphI), BbvI (Bst71I), BcefI, BseMII, BseXI, BspPI, BstF5I (BseGI, FokI), FauI, HgaI, MboII, PleI, SfaNI, and TspRI. The following class IIS enzymes that recognize a six-base contiguous sequence can also be used: AceIII, BbsI (BbvII, BpiI, BpuAI), Bce83I, BctVI, BfiI (BmrI), BfuI, BpmI (GsuI), BsaI (Eco31I), BseRI, BsgI, BsmBI (Esp3I), BsmFI, BspMI, BsrDI (Bse3DI), Bsu6I (Eam1104I, EarI, Ksp632I), Eco57I, FauI, MmeI, RleAI, TaqII, and Tth111II. SapI, which recognizes a seven-base sequence, is also useful for the presently described methods. Additional suitable class IIS restriction enzymes are known to those of skill in the art (see, for example, Szybalski et al., *Gene* 100:13 (1991)).

As an illustration, Example 1 describes a study in which two exons were amplified from genomic DNA using sense and antisense polymerase chain reaction primers. The genomic template is represented below, in which intron nucleotide sequences are presented in lower case, and nucleotide sequences (SEQ ID NOS.:9–12) encoding indicated amino acid residues of the amino acid sequence (SEQ ID NO:13) are grouped as codons:

```
   E   A   M  |—————— G ——————|  D   T   F
...GAG GCT ATG Ggt...{intron}...agGA GAT ACC TTC...
...CTC GCA TAC Cca...{intron}...tcCT CTA TGG AGG...
         Exon 1                        Exon 2.
```

In this study, each of the primers included an Eco31I class IIS recognition site. The Eco31I recognition site, like that of most class IIS endonucleases, is nonpalindromic. The orientation of the recognition site will determine whether Eco31I cleaves a DNA molecule upstream or downstream of its recognition site, or generates suitable complementary ends. The two orientations of the Eco31I recognition site will be cleaved in the following manner, where "N" is any nucleotide:

5' ... GGTCTCN↑NNNNN ... 3'     (SEQ ID NO:7)

3' ... CCAGAGNNNNN↑N ... 5'     (SEQ ID NO:8)

or

5' ... N↑NNNNNGAGACC ... 3'     (SEQ ID NO:14)

3' ... NNNNN↑NCTCTGG ... 5'     (SEQ ID NO:15).

Since each exon of the illustrative genomic template was amplified with primer pairs that included Eco31I recognition sites, each amplified exon could be cleaved by Eco31I at either end. The cleaved fragments, however, could not self-ligate.

Prior to Eco31I cleavage, the downstream portion of the first exon had the following structure with the indicated cleavage sites, and an underlined Eco31I recognition site:

5' ... CAGGCTATG↑GGAGT<u>GAGACC</u> ... 3'  (SEQ ID NO:16)

3' ... GTCCGATACCCTC↑A<u>CTCTGG</u> ... 5'  (SEQ ID NO:17).

In the exemplary genomic DNA template, the splice junction occurred after the sequence "GCT ATG G" in the sense strand, thus disrupting the coding sequence following the first nucleotide of a codon. In the antisense strand of the amplified product (shown above), the sequence "3' CCTC 5'," which was engineered into the primer, provides the complementary cytidine residue of the disrupted codon and the remaining ("CT") nucleotides of the disrupted codon, as well as a complementary cytidine residue of the next codon.

Before Eco31I cleavage, the upstream portion of the second exon had the following structure with the indicated cleavage sites, and an underlined Eco31I recognition site:

5' ... <u>GGTCTCA</u>↑GGAGATACCTTC ... 3'   (SEQ ID NO:18)

3' ... <u>CCAGAGTCCRC</u>↑TATGGAAG ... 5'   (SEQ ID NO:19).

Here, the first "G" nucleotide located downstream of the cleavage site in the sense strand was specified by the sense primer used to amplify the second exon. The following "GA" nucleotide sequence represents the first two nucleotides of the second exon, as well as the last two nucleotides of the codon disrupted by the intron. Following Eco31I cleavage, the downstream end of the first exon segment and the upstream end of the second exon segment are complementary to each other, and, when joined, provided a seamless coding region:

5'...GCTATG   GGAGATACCTT...3'  (SEQ ID NO:20)

3'...CGATACCCTC   TATGGAA...5'  (SEQ ID NO:21)

↓

```
     A   M   G   D   T             (SEQ ID NO:22)
5'...GCT ATG GGA GAT ACC TT...3'   (SEQ ID NO:20)
3'...CGA TAC CCT CTA TGG AA...5'   (SEQ ID NO:21).
```

A suitable length of an amplification primer can be determined by one skilled in the art. As an illustration, an amplification primer can consist of ten to 100 or more nucleotides, between 15 and 80 nucleotides, between 15 and 60 nucleotides, between 15 and 40 nucleotides, between 15 and 25 nucleotides, and the like. Standard techniques for performing PCR are well-known (see, generally, Mathew (Ed.), *Protocols in Human Molecular Genetics* (Humana Press, Inc. 1991), White (Ed.), *PCR Protocols: Current Methods and Applications* (Humana Press, Inc. 1993), Cotter (Ed.), *Molecular Diagnosis of Cancer* (Humana Press, Inc. 1996), Hanausek and Walaszek (Eds.), *Tumor Marker Protocols* (Humana Press, Inc. 1998), Lo (Ed.), *Clinical Applications of PCR* (Humana Press, Inc. 1998), Meltzer (Ed.), *PCR in Bioanalysis* (Humana Press, Inc. 1998), Kochanowski and Reischl (Eds.), *Quantitative PCR Protocols* (Humana Press, Inc. 1999), and Rapley (Ed.), *The Nucleic Acids Protocol Handbook* (Humana Press, Inc. 2000)). In addition, other suitable amplification methods are known to those of skill in the art, such as nucleic acid sequence based amplification, self-sustained sequence amplification, restriction amplification, strand displacement amplification, and the like (see, for example, Fahy et al., *PCR Methods and Applications* 1:25 (1991); Walker et al., *Proc. Nat'l. Acad. Sci. USA* 89:392 (1992); Sooknanan and Malek, *Biotechnology* 13:563 (1995); Finckh et al. (Eds.), *Methods in DNA Amplification* (Kluwer Academic/Plenum Publishers 1997); Rapley, *The Nucleic Acid Protocols Handbook* (Humana Press, Inc. 2000)).

Following cleavage, restriction enzymes can be inactivated by standard methods, including heat inactivation. Moreover, these enzymes can be removed from a mixture containing a cleaved DNA molecule by extraction with organic solutions, such as a phenol/chloroform solution and the like. General methods for ligating nucleic acid molecules are known to those of skill in the art. See, for example, Ausubel et al. (eds.), *Short Protocols in Molecular Biology*, 3$^{rd}$ Edition (John Wiley & Sons 1995).

Example 1 illustrates a means to generate a continuous amino acid-encoding sequence from a nucleotide template that comprises two noncontiguous amino acid-encoding sequences. However, the methods described herein can be used to generate a continuous amino acid-encoding sequence from a template containing any number of noncontiguous amino acid encoding sequences. For example, each of two or more exons can be amplified and treated with a class IIS restriction endonuclease in a separate container, and the cleaved fragments can then be ligated to produce a complete amino acid-encoding nucleic acid molecule.

More generally, the strategy of the present invention can be applied in a variety of uses. As an illustration, the approaches described herein can be used to produce fusion proteins devoid of undesired amino acids, to generate proteins that include repeating motifs of interest, and to produce proteins that contain useful mutations or that lack undesired mutations. Such undesired mutations may arise during the construction of a genomic or cDNA library, during nucleic acid molecule amplification, or may occur as variants within a population. In addition, the presently described methods can be used to produce nucleic acid molecules comprising two or more nucleotide sequences that control gene expression. For example, a nucleic acid molecule can be produced that comprises a regulatory element and a promoter derived from different genes. Moreover, the methods of the present invention can be used to produce nucleic acid molecules comprising at least one nucleotide sequence that controls gene expression, and at least one nucleotide sequence that encodes an amino acid sequence. As an illustration, a nucleic acid molecule can be produced that comprises an exon from one gene, and a regulatory element, or a downstream expression control element, from another gene. An example of a downstream expression control element is a nucleotide sequence that enhances mRNA stability. Those of skill in the art can devise other uses that take advantage of the methods described herein.

The methods of the present invention can also be used to generate continuous coding sequence containing one or more mutations from a genomic nucleotide sequence, or other templates, by the ordered ligation of amplified DNA segments, wherein one or more segments contain desired nucleotide mutations. In this way, it is possible to produce specific nucleotide alterations to a continuous coding sequence. A coding sequence with such alterations may encode a polypeptide with new useful functions.

The methods of the present invention can also be used to restore gene function rendered inactive by naturally occurring mutations to produce proteins with useful functions. One class of inactive genes, the so-called genomic pseudo-genes, are members of multigene families, in which members have accumulated inactivating mutations during evolution and subsequent radiation. Pseudo-gene defects include: nucleotide substitutions leading to the coding of an inactive polypeptide or the creation of a premature translation termination codon; deletion or insertion of nucleotides resulting in an altered coding frame; or mutation of the mRNA splice sites leading to aberrant mRNA processing. Pseudo-gene mutations that are targets for restoration using the methods of the present invention can be identified by comparing the nucleotide sequences of the pseudo-genes with those of active members of the gene family. These mutations can be treated as disruptions in the coding sequence, and are corrected following the approach for removal of introns, as detailed herein.

Methods for the generation of nucleotide mutations in amplified nucleic acid products are known in the art. One particularly useful approach is to incorporate the desired nucleotide alteration in primers used for nucleic acid amplification. Such sequence alteration would include the addition or deletion of nucleotides, or the substitution of any given nucleotide or nucleotides, which result in alteration of amino acid coding sequence, expression, or regulatory activity of properties of a nucleic acid segment. Those skilled in the art can design primers with the desired mutation(s) without undo impairment of the priming activity of the primers used in the amplification reaction. In general, the amplification priming activity of the primer is not impaired when sequence alteration is made away from the 3' ends of the primer. Typically, an uninterrupted stretch of at least 10 to 15 nucleotides, and preferably 15 to 20 or more nucleotides, at the 3' end of a primer can provide an efficient and specific amplification of the template. The resulting amplified product from such a primer would incorporate the desired sequence alteration.

B. Expression Vectors

The methods of the present invention can be used to produce polypeptides having value in industry, therapeutics, diagnostics, or research. Illustrative proteins include antibodies and antibody fragments, receptors, immunomodulators, hormones, and the like. For example, an expression vector can include a nucleic acid molecule that encodes a pharmaceutically active molecule, such as Factor VIIa, proinsulin, insulin, follicle stimulating hormone, tissue type plasminogen activator, tumor necrosis factor, interleukins (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21), colony stimulating factors (e.g., granulocyte-colony stimulating factor, and granulocyte macrophage-colony stimulating factor), interferons (e.g., interferons-$\alpha$, -$\beta$, -$\gamma$, -$\omega$, -$\delta$, -$\tau$, and $\epsilon$), a stem cell growth factor, erythropoietin, and thrombopoietin. Additional examples of a protein of interest include an antibody, an antibody fragment, an anti-idiotype antibody (or, fragment thereof), a chimeric antibody, a humanized antibody, an antibody fusion protein, and the like.

Expression vectors that are suitable for production of an amino acid sequence of interest in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; (3) DNA elements that control the processing of transcripts, such as a transcription termination/polyadenylation sequence; and (4) a selectable marker gene for eukaryotic cells. As discussed above, expression vectors can also include nucleotide sequences encoding a secretory sequence, that directs the heterologous polypeptide into the secretory pathway of a host cell. Moreover, vectors for high level expression in yeast can include targeting sequences to promote homologous recombination in host genomic DNA.

Recombinant host cells can be produced that secrete the amino acid sequence of interest into surrounding medium. Accordingly, the present invention contemplates expression vectors comprising a nucleotide sequence that encodes a secretory signal sequence, which is also known as a "signal peptide," a "leader sequence," a "prepro sequence," or a "pre sequence." The secretory signal sequence is operably linked to a gene of interest such that the two sequences are joined in the correct reading frame and positioned to direct the newly synthesized polypeptide of interest into the secretory pathway of the host cell. Secretory signal sequences are commonly positioned 5' to the nucleotide sequence encoding the amino acid sequence of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of a protein produced by mammalian cells (e.g., tissue-type plasminogen activator signal sequence, as described, for example, in U.S. Pat. No. 5,641,655) is useful for expression of gene of interest in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach*, 2$^{nd}$ Edition, Glover and Hames (eds.), pages 123–167 (Oxford University Press 1995).

Expression vectors can also comprise nucleotide sequences that encode a peptide tag to aid the purification of the polypeptide of interest. Peptide tags that are useful for isolating recombinant polypeptides include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

A wide variety of selectable marker genes are available (see, for example, Kaufman, *Meth. Enzymol.* 185:487 (1990); Kaufman, *Meth. Enzymol.* 185:537 (1990)). For example, one suitable selectable marker is a gene that provides resistance to the antibiotic neomycin. In this case, selection is carried out in the presence of a neomycin-type drug, such as G418 or the like. Bleomycin-resistance genes, such as the Sh ble gene, are also useful selectable marker genes for the presently described methods. These genes produce a protein that inhibits the activity of bleomycin/phleomycin-type drugs, such as ZEOCIN (Gatignol et al., *Mol. Gen. Genet.* 207:342 (1987); Drocourt et al., *Nucl. Acids Res.* 18:4009 (1990)). ZEOCIN is toxic in a broad range of cell types, including bacteria, fungi, plant, avian, insect, and mammalian cells. Additional selectable markers include hygromycin B-phosphotransferase, the AUR1 gene product, adenosine deaminase, aminoglycoside phosphotransferase, dihydrofolate reductase, thynidine kinase, and xanthinc-guanine phosphoribosyltransferase (see, for example, Srivastava and Schlessinger, *Gene* 103:53 (1991); Romanos et al., "Expression of Cloned Genes in Yeast," in *DNA Cloning 2: Expression Systems*, 2$^{nd}$ Edition, pages 123–167 (IRL Press 1995); Markie, *Methods Mol. Biol.* 54:359 (1996); Pfeifer et al., *Gene* 188:183 (1997); Tucker and Burke, *Gene* 199:25 (1997); Hashida-Okado et al., *FEBS Letters* 425:117 (1998)). Selectable marker genes can be cloned or synthesized using published nucleotide sequences, or marker genes can be obtained commercially.

Another type of selectable marker gene is a gene that produces a readily detectable protein, such as green fluorescent protein, red fluorescent protein, an enzyme (e.g., placental alkaline phosphatase), or a cell surface protein that can be detected with an antibody (e.g. CD4, CD8, Class I major histocompatibility complex (MHC) protein, etc.). The expression products of such selectable marker genes can be used to sort transfected cells from untransfected cells by such standard means as FACS sorting or magnetic bead separation technology.

To express a gene of interest or a selectable marker gene, a nucleic acid molecule encoding the amino acid sequence must be operably linked to regulatory sequences that control transcriptional expression and then, introduced into a host cell. In addition to transcriptional regulatory sequences, such as promoters and enhancers, expression vectors can include transcriptional and translational regulatory sequences. For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Suitable transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996)).

Alternatively, a prokaryotic promoter, such as the bacteriophage T3 RNA polymerase promoter, can be used to control expression of the gene of interest in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

It may be advantageous for recombinant host cells to express certain selectable marker gene products on the cell surface. For example, green fluorescent protein can be expressed on the cell surface. Various approaches can be used to achieve surface display by producing fusion proteins that contain the selectable marker protein and a transmembrane domain from another protein to anchor the fusion protein to the cell membrane. As an illustration, pDisplay™ is a commercially available vector that is used to display a polypeptide on the surface of a mammalian cell (INVITROGEN Corp.; Carlsbad, Calif.). In this vector, a multiple cloning site resides between sequences that encode two identifiable peptides, hemagglutinin A and myc epitopes. The vector also includes sequences that encode an N-terminal signal peptide derived from a murine irnmunoglobulin κ-chain, and a type I transmembrane domain of platelet-derived growth factor receptor, located at the C-terminus. In this way, a selectable marker gene product is expressed by a transfected cell as an extracellular fusion protein, anchored to the plasma membrane at the fusion protein C-terninus by the transmembrane domain.

Alternatively, a type II signal anchor domain-encoding nucleotide sequence can be used to provide surface display of the selectable marker gene product. Examples of type II cell surface proteins that comprise such signal anchor domains include influenza neurarminidase, the small hydrophobic proteins of the paramyxovirus simian virus, the pararnyxovirus hemagglutinin-neuraminidase, human and rat asialoglycoprotein receptors, chicken hepatic lectin, human and rabbit neutral endopeptidase, human intestinal amninopeptidase, rabbit sucrase-isomaltase receptor, human transferrin receptor, hepatic glycoprotein receptor, human IgE receptor, murine 1,4-β-galactosyltransferase, human P-glycoprotein receptor, human invariant chains of class II histocompatibility antigens, rat sodium channel proteins, rat brain, muscle and liver glucose transporter proteins, bacterial leader peptidase, and members of the tumor necrosis factor/nerve growth factor superfamily (see, for example, Wolfe et al., *J. Biol. Chem.* 258:12073 (1983); Chiacchi and Drickamer, *J. Biol. Chem.* 259:15440 (1984); Hiebert et al., *J. Virol.* 54:1 (1985); Hiebert et al., *J. Virol.* 55:744 (1985); Schneider et al., *Nature* 311:675 (1984); Spiess and Lodish, *Proc. Nat'l Acad. Sci. USA* 82:6465 (1985); Strubin et al., *EMBO J.* 3:869 (1984); Semenza, *Annu. Rev. Cell Biol.* 2:255 (1986); Lipp and Dobberstein, *J. Cell Biol.* 106:1813 (1988); Hartmann et al., *Proc. Nat'l Acad. Sci. USA* 86:5786 (1989)). Moreover, Chou and Elrod, *Proteins: Structure, Function, and Genetics* 34:137 (1999), disclose 152 type II membrane proteins, which they used to devise a method for predicting whether an amino acid sequence confers the type II membrane protein structure.

After constructing the expression vector comprising the amino acid-encoding sequences of interest, the vector is typically propagated in a host cell. Vector propagation is conveniently carried out in a prokaryotic host cell, such as *E. coli* or *Bacillus subtilus*. Suitable strains of *E. coli* include BL21(DE3), BL21(DE3)pLysS, BL21(DE3)pLysE, DH1, DH4I, DH5, DH5I, DH5IF, DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel et al. (eds.), *Short Protocols in Molecular Biology*, 3rd Edition (John Wiley & Sons 1995) ["Ausubel 1995"]; Wu et al., *Methods in Gene Biotechnology* (CRC Press, Inc. 1997)).

4. Production of Recombinant Polypeptides by Host Cells

The amino acid sequence of interest may be expressed in any prokaryotic or eukaryotic host cell. Preferably, the amino acid sequence of interest is produced by a eukaryotic cell, such as a mammalian cell, fungal cell, plant cell, insect cell, avian cell, and the like. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570, ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

An expression vector can be introduced into host cells using a variety of standard techniques including calcium phosphate transfection, liposome-mediated transfection, microprojectile-mediated delivery, electroporation, and the like. Transfected cells can be selected and propagated to provide recombinant host cells that comprise the gene of interest stably integrated in the host cell genome.

The baculovirus system provides an efficient means to introduce cloned genes of interest into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the polypeptide of interest into a baculovirus genome maintained in *E. coli* as a large plasmid called a "bacemid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed polypeptide, for example, a Glu-Glu epitope tag (Grussenmeyer et al., *Proc. Nat'l Acad. Sci.* 82:7952 (1985)). Using a technique known in the art, a transfer vector containing a gene of interest is transformed into *E. coli*, and screened for bacmids, which contain an interrupted lacZ gene indicative of recombinant baculovirus. The bacmid DNA containing the recombinant baculovirus genome is then isolated using common techniques.

The recombinant virus or bacinid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as Drosophila Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2–5×10$^5$ cells to a density of 1–2×10$^6$ cells at which time a recombinant viral stock is added at a multiplicity of infection of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147–168 (The Humana Press, Inc. 1991), by Patel et al., "The baculovirus expression system," in *DNA Cloning 2: Expression Systems, 2nd Edition*, Glover et al. (eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc. 1996).

Fungal cells, including yeast cells, can also be used to express the genes of interest. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transforrned cells are selected by phenotype determined by the selectable marker, commonly drug resistance or the ability to grow in the absence of a particular nutrient (e.g., leucine). An illustrative vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986), and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formnate dehydrogenase (FMD), and catalase (CAT) genes. To facilitate integration of the DNA into the host chromosome, it is preferred to have the entire expression segment of the plasmid flanked at both ends by host DNA sequences. For large-scale, industrial processes where it is desirable to minimize the use of methanol host cells can be used in which both methanol utilization genes (AUG1 and AUG2) are deleted. For production of secreted proteins, host cells can be used that are deficient in vacuolar protease genes (PEP4 and PRB1). Electroporation is used to facilitate the introduction of a plasmid containing DNA encoding a polypeptide of interest into *P. methanolica* cells. *P. methanolica* cells can be taansformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing nucleic acid molecules into plant tissue include the direct infection or co-cultivation of plant tissue with *Agrobacterium tumefaciens*, microprojectile-mediated delivery, DNA injection, electroporation, and the like. See, for example, Horsch et al., Science 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67–88 (CRC Press, 1993).

Standard methods for introducing nucleic acid molecules into bacterial, yeast, insect, mammalian, and plant cells are provided, for example, by Ausubel (1995). General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Established methods for isolating recombinant proteins from a baculovirus system are described by Richardson (ed.), *Baculovirus Expression Protocols* (The Humana Press, Inc. 1995).

The present invention, thus generally described, will be understood more readily by reference to the following example, which is provided by way of illustration and are not intended to be limiting of the present invention.

EXAMPLE 1

Conversion of Noncontiguous Genomic Sequences into a Contiguous Coding Sequence

A genomic bacterial artificial chromosome (BAC) clone was obtained, which was believed to contain nucleotide sequences of a new gene. DNA from the clone was prepared for use as a PCR template sequence using an AutoGen 740 automated DNA extraction system in accordance with the manufacturer's instructions (AutoGen, Framingham, Mass.). Nucleotide sequence analysis indicated the new gene, designated as "Ztest1," comprised two exons, each with conserved structural motifs that were characteristic of the rclaxin family of polypeptides. The predicted intron exon junctions contained consensus splice sequences. A Ztest1 exon 1 DNA segment was synthesized using the following sense and antisense PCR primers, in which recognition sites for the class IIS restriction endonuclease, Eco31I, are underlined: 5' TGAA GAA <u>GGTCTC</u> GAATTC GTC GAC ACC ATG GCC AGG TAC ATG CTG CTG CTG CTC 3' (ZC27563; SEQ ID NO:1), and 5' TGAA GAA <u>GGTCTC</u> AC TCC CAT AGC CTC GTG GGC CAG GAT GTC TGA 3' (ZC27565; SEQ ID NO:2). A Ztest1 exon 2 DNA segment was synthesized using the following sense and antisense PCR primers: 5' TGAAGAA <u>GGTCTC</u> A GGA GAT ACC TTC CCG GAT GCA GAT GCT 3' (ZC27566; SEQ ID NO:3), and 5' TGAAGAA <u>GGTCTC</u> TCTAGA ACT CTA GCA AAG GCT ACT GAT TTC ACT TIT GCT 3' (ZC27566; SEQ ID NO:4). DNA amplification was carried out in a 100 µl reaction volume containing: 10 µl 10X native PFU DNA polymerase buffer (Stratagene; La Jolla, Calif.), 1 µl of 20 mM dNTP mix, 30 pmoles each of sense and antisense primers, 10 ng of the BAC clone DNA template, and 2 units of native PFU DNA polymerase (Stratagene). DNA amplification was carried out as follows: one cycle at 95° C. for one minute, followed by three cycles at 95° C. for 10 seconds, 45° C. for 10 seconds, 72° C. for two minutes, followed by 17 cycles at 95° C. for 10 seconds, 60° C. for 10 seconds, 72° C. for two minutes, followed by a further five minutes at 72° C. The amplified exon products were extracted with phenol and chloroform, and then were precipitated with ethanol. The PCR products were digested with Eco31I according to the instruction of the vendor (MBI Fermentas, Inc.; Amherst, N.Y.).

The exon fragments were ligated into an EcoRI and XbaI digested mammalian expression vector in a 5 µl ligation reaction, which consisted of: 1 µl vector (40 ng), 0.5 µl 10X Promega ligase buffer (Promega Corporation; Madison, Wis.), 0.5 µl 10 mM ATP, 1 µl Eco31I digested Ztest1 exon 1 (about 10 ng), 1 µl Eco31I digested Ztest1 exon 2 (about 10 ng), and 0.5 µl (15 units/µl) T4 DNA Ligase (Promega Corporation). The ligation reaction was carried at 6° C. for two hours, 8° C. for two hours, 10° C. for two hours, 12.5° C. for two hours, 15° C. for two hours, followed by an overnight incubation at 10° C. One microliter of the ligation mixture was used to transform MAX efficiency DH10B competent cells (Life Technologies, Inc.; Rockville, Md.). Transfornants were selected by plating onto Ampicilin LB agar plates. The resulting clone carrying the Ztest1 coding sequence was confirmed by DNA sequencing.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for producing a nucleic acid molecule that comprises a continuous nucleotide sequence capable of being transcribed and translated to produce a protein of interest, the nucleic acid molecule derived from noncontiguous nucleotide sequences, comprising:

(a) amplifying at least two nucleotide sequences from a single nucleic acid molecule template using primer pairs to produce double-stranded amplified products, wherein the amplified nucleotide sequences reside noncontiguously in the nucleic acid molecule template, wherein each primer of a primer pair comprises an uninterrupted recognition sequence for a class IIS restriction endonucicase which is located near the 5'-end of the primer and a portion of an amino acid coding sequence, such that cleavage of the amplified products with the class IIS restriction endonuclease yields at least two nucleic acid molecule fragments with cohesive ends that, when ligated to each other, produce a continuous nucleotide sequence capable of being transcribed and translated to produce a protein of interest, (b) cleaving amplified products with the class IIS restriction endonuclease to produce nucleic acid molecule fragments, and (c) ligating cleaved nucleic acid molecule fragments to produce a nucleic acid molecule comprising the continuous nucleotide sequence capable of being transcribed and translated to produce a protein of interest.

2. A method for producing a nucleic acid molecule that comprises a continuous nucleofide sequence capable of being transcribed and translated to produce a protein of interest, the nucleic acid molecule derived from nonconziguous nucleolide sequences, comprising:

(a) amplifying at least two nucleotide sequences from at least two nucleic acid molecule templates using primer pairs to produce double-stranded amplified products, wherein at least one primer of a primer pair comprises an uninterrupted recognition sequence for a class IIS restriction endonuciease which is located near the 5'-end of the primer and a portion of an amino acid coding sequence, such that cleavage of the amplified products with the class IIS restriction endonuclease yields at least two nucleic acid molecule fragments with cohesive ends that, when ligated to each other, produce a continuous nucleotide sequence capable of being transcribed and translated to produce a protein of interest, (b) cleaving amplified products with the class IIS restriction endonuclease to produce nucleic acid molecule fragments, and (c) ligating cleaved nucleic acid molecule fragments to produce a nucleic acid molecule comprising the continuous nucleotide sequence capable of being transcribed and translatcd to produce a protein of interest.

3. The method of claim 1, wherein the class IIS restriction endonuclease recognizes a five-base uninterrupted recognition sequence.

4. The method of claim 3, wherein the class IIS restriction endonuclease is selected from the group consisting of AclWI, Alw26I, AlwI, AsuHPI, BbvI, BcefI, BinI, BseGI, BseMII, BseXI, BspPl, BsmAI, Bst7II, BstF5I, FauI, FokI, HgaI, HphI, MboI, PleII, SfaNI, and TspRI.

5. The method of claim 1, wherein the class IIS restriction endonuclease recognizes a six-base uninterruptcd recognition sequence.

6. The method of claim 5 wherein the class IIS restriction endonuclesse is selected from the group consisting of AceIII, BbsI, BbvII, Bce83I, BciVI, BfiI, BfuI, BmrI, BpiI, BpmI, BpuAI, BsaI, Bse3DI, BseRI, BsgI, BsmBI, BsmFI, BspMI, BsrDI, Bsu6I, EamlI104I, EarI, Eco31I, Eco57I, Esp3I, FauI, GsuI, Ksp632I, MmeI, RleAI, TaqII, and Tthl111II.

7. The method of claim 1, wherein the class IIS restriction endonuclease recognizes a seven-base uninterrupted recognition sequence.

8. The method of claim 7, wherein the class IIS restriction endonuclease is SapI.

9. The method of claim 1, wherein the nucleic acid molecule template is selected from the group consisting of genomic DNA, cDNA, vector DNA, and a chemically-synthesized nucleic acid molecule.

10. The method of claim 2, wherein at least one nucleic acid molecule template is selected from the group consisting of genomic DNA, cDNA, vector DNA, and a chemically-synthesized nucilic acid molecule.

11. The method of claim 1, wherein each of the amplified products comprises at least a portion of an exon.

12. The method of claim 1, wherein at least one of the amplified products comprises at least a portion of an exon, and at least one of the amplified products comprises a nucleotidc sequence capable of controlling gene expression.

13. The method of claim 1, wherein each of the amplified products comprises an exon.

14. The method of claim 13, wherein one primer of each primer pair is partially complementary to the antisense strand of the 5' end of an exon, and wherein the other primer of each primer pair is partially complementary to the sense strand of the 3'-end of the exon.

15. The method of claim 1 wherein at least one of the amplified products comprises at least one mutation of the nucleotide sequence, which resides in the corresponding nucleic acid molecule template.

16. The method of claim 18, wherein at least one mutation resides in an amino acid encoding sequence.

17. The method of claim 1, wherein the act of amplification is performed using a polymerase chain reaction.

* * * * *

SEQUENCE LISTING

```
<160> NUMBER OF SEQ ID NOS: 22

<210> SEQ ID NO 1
<211> LENGTH: 55
<212> TYPE: DNA
<213> ORGANISM: Artificial Sequence
<220> FEATURE:
<223> OTHER INFORMATION: PCR primer.

<400> SEQUENCE: 1
tgaagaaggt ctcgaattcg tcgacaccat ggccaggtac atgctgctgc tgctc         55

<210> SEQ ID NO 2
<211> LENGTH: 45
<212> TYPE: DNA
<213> ORGANISM: Artificial Sequence
<220> FEATURE:
<223> OTHER INFORMATION: PCR primer.

<400> SEQUENCE: 2
tgaagaaggt ctcactccca tagcctcgtg ggccaggatg tctga                    45

<210> SEQ ID NO 3
<211> LENGTH: 41
<212> TYPE: DNA
<213> ORGANISM: Artificial Sequence
<220> FEATURE:
<223> OTHER INFORMATION: PCR primer.

<400> SEQUENCE: 3
tgaagaaggt ctcaggagat accttcccgg atgcagatgc t                        41

<210> SEQ ID NO 4
<211> LENGTH: 52
<212> TYPE: DNA
<213> ORGANISM: Artificial Sequence
<220> FEATURE:
<223> OTHER INFORMATION: PCR primer.

<400> SEQUENCE: 4
tgaagaaggt ctctctagaa ctctagcaaa ggctactgat ttcacttttg ct            52

<210> SEQ ID NO 5
<211> LENGTH: 12
<212> TYPE: DNA
```

```
<213> ORGANISM: Artificial Sequence
<220> FEATURE:
<223> OTHER INFORMATION: Illustrative nucleotide sequence.
<221> NAME/KEY: misc_feature
<222> LOCATION: 4, 5, 6, 7, 8, 9
<223> OTHER INFORMATION: n = A,T,C or G

<400> SEQUENCE: 5
ccannnnnnt gg                                                              12

<210> SEQ ID NO 6
<211> LENGTH: 12
<212> TYPE: DNA
<213> ORGANISM: Artificial Sequence
<220> FEATURE:
<223> OTHER INFORMATION: Illustrative nucleotide sequence.
<221> NAME/KEY: misc_feature
<222> LOCATION: 4, 5, 6, 7, 8, 9
<223> OTHER INFORMATION: n = A,T,C or G

<400> SEQUENCE: 6
ggtnnnnnna cc                                                              12

<210> SEQ ID NO 7
<211> LENGTH: 12
<212> TYPE: DNA
<213> ORGANISM: Artificial Sequence
<220> FEATURE:
<223> OTHER INFORMATION: Illustrative nucleotide sequence.
<221> NAME/KEY: misc_feature
<222> LOCATION: 7, 8, 9, 10, 11, 12
<223> OTHER INFORMATION: n = A,T,C or G

<400> SEQUENCE: 7
ggtctcnnnn nn                                                              12

<210> SEQ ID NO 8
<211> LENGTH: 12
<212> TYPE: DNA
<213> ORGANISM: Artificial Sequence
<220> FEATURE:
<223> OTHER INFORMATION: Illustrative nucleotide sequence.
<221> NAME/KEY: misc_feature
<222> LOCATION: 7, 8, 9, 10, 11, 12
<223> OTHER INFORMATION: n = A,T,C or G

<400> SEQUENCE: 8
ccagagnnnn nn                                                              12

<210> SEQ ID NO 9
<211> LENGTH: 12
<212> TYPE: DNA
<213> ORGANISM: Artificial Sequence
<220> FEATURE:
<223> OTHER INFORMATION: Illustrative nucleotide sequence.

<400> SEQUENCE: 9
gaggctatgg gt                                                              12

<210> SEQ ID NO 10
<211> LENGTH: 13
<212> TYPE: DNA
<213> ORGANISM: Artificial Sequence
<220> FEATURE:
<223> OTHER INFORMATION: Illustrative nucleotide sequence.

<400> SEQUENCE: 10
aggagatacc ttc                                                             13
```

<210> SEQ ID NO 11
<211> LENGTH: 12
<212> TYPE: DNA
<213> ORGANISM: Artificial Sequence
<220> FEATURE:
<223> OTHER INFORMATION: Illustrative nucleotide sequence.

<400> SEQUENCE: 11
ctcgcatacc ca                                                              12

<210> SEQ ID NO 12
<211> LENGTH: 13
<212> TYPE: DNA
<213> ORGANISM: Artificial Sequence
<220> FEATURE:
<223> OTHER INFORMATION: Illustrative nucleotide sequence.

<400> SEQUENCE: 12
tcctctatgg aag                                                             13

<210> SEQ ID NO 13
<211> LENGTH: 7
<212> TYPE: PRT
<213> ORGANISM: Artificial Sequence
<220> FEATURE:
<223> OTHER INFORMATION: Illustrative amino acid sequence.

<400> SEQUENCE: 13

Glu Ala Met Gly Asp Thr Phe
 1               5

<210> SEQ ID NO 14
<211> LENGTH: 12
<212> TYPE: DNA
<213> ORGANISM: Artificial Sequence
<220> FEATURE:
<223> OTHER INFORMATION: Illustrative nucleotide sequence.
<221> NAME/KEY: misc_feature
<222> LOCATION: 1, 2, 3, 4, 5, 6
<223> OTHER INFORMATION: n = A,T,C or G

<400> SEQUENCE: 14
nnnnnngaga cc                                                              12

<210> SEQ ID NO 15
<211> LENGTH: 12
<212> TYPE: DNA
<213> ORGANISM: Artificial Sequence
<220> FEATURE:
<223> OTHER INFORMATION: Illustrative nucleotide sequence.
<221> NAME/KEY: misc_feature
<222> LOCATION: 1, 2, 3, 4, 5, 6
<223> OTHER INFORMATION: n = A,T,C or G

<400> SEQUENCE: 15
nnnnnnctct gg                                                              12

<210> SEQ ID NO 16
<211> LENGTH: 20
<212> TYPE: DNA
<213> ORGANISM: Artificial Sequence
<220> FEATURE:
<223> OTHER INFORMATION: Illustrative nucleotide sequence.

<400> SEQUENCE: 16
caggctatgg gagtgagacc                                                      20

```
<210> SEQ ID NO 17
<211> LENGTH: 20
<212> TYPE: DNA
<213> ORGANISM: Artificial Sequence
<220> FEATURE:
<223> OTHER INFORMATION: Illustrative nucleotide sequence.

<400> SEQUENCE: 17
gtccgatacc ctcactctgg                                              20

<210> SEQ ID NO 18
<211> LENGTH: 19
<212> TYPE: DNA
<213> ORGANISM: Artificial Sequence
<220> FEATURE:
<223> OTHER INFORMATION: Illustrative nucleotide sequence.

<400> SEQUENCE: 18
ggtctcagga gataccttc                                               19

<210> SEQ ID NO 19
<211> LENGTH: 19
<212> TYPE: DNA
<213> ORGANISM: Artificial Sequence
<220> FEATURE:
<223> OTHER INFORMATION: Illustrative nucleotide sequence.

<400> SEQUENCE: 19
ccagagtcct ctatggaag                                               19

<210> SEQ ID NO 20
<211> LENGTH: 17
<212> TYPE: DNA
<213> ORGANISM: Artificial Sequence
<220> FEATURE:
<223> OTHER INFORMATION: Illustrative nucleotide sequence.

<400> SEQUENCE: 20
gctatgggag atacctt                                                 17

<210> SEQ ID NO 21
<211> LENGTH: 17
<212> TYPE: DNA
<213> ORGANISM: Artificial Sequence
<220> FEATURE:
<223> OTHER INFORMATION: Illustrative nucleotide sequence.

<400> SEQUENCE: 21
cgataccctc tatggaa                                                 17

<210> SEQ ID NO 22
<211> LENGTH: 5
<212> TYPE: PRT
<213> ORGANISM: Artificial Sequence
<220> FEATURE:
<223> OTHER INFORMATION: Illustrative amino acid sequence.

<400> SEQUENCE: 22

Ala Met Gly Asp Thr
 1               5
```